United States Patent [19]

Horwell et al.

[11] Patent Number: 5,929,088
[45] Date of Patent: Jul. 27, 1999

[54] CYCLIC AMINO ACIDS AS PHARMACEUTICAL AGENTS

[75] Inventors: David C. Horwell, Foxton; Justin S. Bryans, Balsham; Clare O. Kneen, Little Walden; Giles Ratcliffe, Hertfordshire, all of United Kingdom

[73] Assignee: Warner-Lambert Company, Morris Plains, N.J.

[21] Appl. No.: 09/077,053

[22] PCT Filed: Jan. 2, 1997

[86] PCT No.: PCT/US97/00255

§ 371 Date: May 18, 1998

§ 102(e) Date: May 18, 1998

[87] PCT Pub. No.: WO97/29101

PCT Pub. Date: Aug. 14, 1997

Related U.S. Application Data

[60] Provisional application No. 60/011,278, Feb. 7, 1996.

[51] Int. Cl.[6] .......... A61K 31/445; A61K 31/38; A61K 31/35; C07D 211/32
[52] U.S. Cl. .......... 514/315; 514/317; 514/331; 514/432; 514/459; 546/235; 546/245; 546/246; 549/13; 549/28; 549/426
[58] Field of Search .......... 514/432, 459, 514/317, 331, 315; 549/28.13, 426; 546/235, 245, 246

[56] References Cited

U.S. PATENT DOCUMENTS

| | | | |
|---|---|---|---|
| 4,024,175 | 5/1977 | Satzinger et al. | 260/468 J |
| 4,087,544 | 5/1978 | Satzinger et al. | 424/305 |
| 5,270,317 | 12/1993 | Bernhart et al. | 514/269 |
| 5,352,788 | 10/1994 | Bernhart et al. | 544/319 |
| 5,491,152 | 2/1996 | Wilde et al. | 514/336 |
| 5,504,056 | 4/1996 | Adachi et al. | 504/248 |
| 5,527,194 | 6/1996 | Rakhit et al. | 514/315 |
| 5,760,006 | 6/1998 | Shank et al. | 514/23 |
| 5,763,460 | 6/1998 | Cliffe et al. | 514/326 |
| 5,849,784 | 12/1998 | Bertenshaw et al. | 514/432 |

OTHER PUBLICATIONS

Smith et al., "New Spiropiperidines as Potent and Selective Non–Peptide Tachykinin NK2 Receptor Antagonists", *J. Med. Chem.*, vol. 38, No. 19, 1995, pp. 3772–3779.

*Primary Examiner*—Deborah C. Lambkin
*Attorney, Agent, or Firm*—Elizabeth M. Anderson

[57] ABSTRACT

Novel cyclic amino acids of formula (Ia) or (Ib) are disclosed and are useful as agents in the treatment of epilepsy, faintness attacks, hypokinesia, cranial disorders, neurodegenerative disorders, depression, anxiety, panic, pain, and neuropathological disorders. Processes for the preparation and intermediates useful in the preparation are also disclosed:

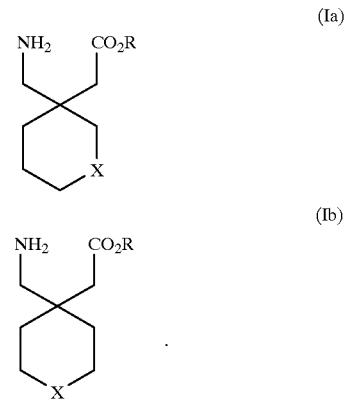

20 Claims, No Drawings

CYCLIC AMINO ACIDS AS PHARMACEUTICAL AGENTS

This application is a 371 of PCT/US97/00255 Jan. 2, 1997 which claims benefit of provisional application No. 60/011,278 Feb. 7, 1996.

BACKGROUND OF THE INVENTION

Compounds of formula $$H_2N-CH_2-\underset{(CH_2)_n}{C}-CH_2-COOR_1$$

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

U.S. Pat. No. 5,270,317 and its divisional U.S. Pat. No. 5,352,788 disclose compounds of formula in which:

$R_1$ and $R_2$ are similar or different and are each independently hydrogen or a group selected from a $C_1$–$C_6$ alkyl, a $C_1$–$C_4$ alkoxy, an amino, an aminomethyl, a carboxyl, an alkoxycarbonyl in which the alkoxy is $C_1$–$C_4$, a cyano, a tetrazolyl, a methyltetrazolyl, a methylsulfonylamino, a trifluoromethylsulfonylamino, a trifluoromethylsulfonylaminomethyl, an N-cyanoacetamide, an N-hydroxyacetamide, an N-(4-carboxy-1,3-thiazol-2-yl)acetamide, a ureido, a 2-cyanoguanidinocarbonyl, a 2-cyanoguanidinomethyl, an imidazol-1-yl-carbonyl, and a 3-cyano-2-methylisothioureidomethyl, with the proviso that at least one of the substituents $R_1$ or $R_2$ is other than hydrogen;
  $R_3$ is a hydrogen, a $C_1$–$C_6$ alkyl which is unsubstituted or substituted by one or more halogen atoms, a $C_2$–$C_6$ alkenyl, a $C_3$–$C_7$ cycloalkyl, a phenyl, a phenylalkyl in which the alkyl is $C_1$–$C_3$, or a phenylalkenyl in which the alkenyl is $C_2$–$C_3$, said phenyl groups being unsubstituted, or monosubstituted or polysubstituted by a halogen atom, a $C_1$–$C_4$ alkyl, a $C_1$–$C_4$ halogenoalkyl, a $C_1$–$C_4$ polyhalogenoalkyl, a hydroxyl, or a $C_1$–$C_4$ alkoxy; and either
  $R_4$ and $R_5$ are each independently a $C_1$–$C_6$ alkyl, a phenyl or a phenylalkyl in which the alkyl is $C_1$–$C_3$, said alkyl, phenyl, and phenylalkyl groups being unsubstituted or substituted by one or more halogen atoms or by a group selected from a $C_1$–$C_4$ perfluoroalkyl, a hydroxyl, and a $C_1$–$C_4$ alkoxy;
  or $R_4$ and $R_5$ together form a group of the formula $=CR_7R_8$, in which $R_7$ is hydrogen, a $C_1$–$C_4$ alkyl or a phenyl, and $R_8$ is a $C_1$–$C_4$ alkyl or a phenyl:
  or else $R_4$ and $R_5$ together are either a group of the formula $(CH_2)_n$ or a group of the formula $(CH_2)_p$Y—$(CH_2)_q$, in which Y is either an oxygen atom, or a sulfur atom, or a carbon atom substituted by a $C_1$–$C_4$ alkyl group, a phenyl or a phenylalkyl in which the alkyl is $C_1$–$C_3$, or a group N—$R_6$, in which $R_6$ is a hydrogen, a $C_1$–$C_4$ alkyl, a phenylalkyl in which the alkyl is $C_1$–$C_3$, a $C_1$–$C_4$ alkylcarbonyl, a $C_1$–$C_4$ alkylcarbonyl, a $C_1$–$C_4$ halogenoalkylcarbonyl, a $C_1$–$C_4$ polyhalogeno-alkylcarbonyl, a benzoyl, an alphaaminoacyl or an N-protecting group, or $R_4$ and $R_5$, together with the carbon atom to which they are bonded, form an indane or an adamantane;
  p+q=m;
  n is an integer between 2 and 11; and
  m is an integer between 2 and 5; or
  $R_4$ is a $C_1$–$C_6$ alkyl which is unsubstituted or substituted by one or more halogen atoms; and
  $R_5$ is a cycloalkyl or a cycloalkylmethyl, said cycloalkyl being $C_3$–$C_7$, which is unsubstituted or substituted by one or more halogen atoms:
  or $R_4$ and $R_5$ are each a cyclopropyl;
  X is an oxygen atom or sulfur atom; and
  z and t are zero or one is zero and the other is one; and their salts.

The compounds are disclosed as having the ability to antagonize angiotension II.

J. Med. Chem., 38:3772–3779 (1995) covers the syntheses of spiropiperidines as potent and selective non-peptide tackykinin $NK_2$ receptor antagonists.

SUMMARY

The novel cyclic amino acids, their derivatives and pharmaceutically acceptable salts are useful in a variety of disorders. The disorders include: epilepsy, faintness attacks, hypokinesia, cranial disorders, neurodegenerative disorders, depression, anxiety, panic, pain, and neuropathological disorders.

The compounds are those of formula

I or a pharmaceutically acceptable salt thereof wherein:

X is O, S, S(O), S(O)$_2$, or NR$_1$ wherein R$_1$ is hydrogen, straight or branched alkyl of from 1 to 6 carbon atoms, or benzyl, —C(O)R$_2$ wherein R$_2$ is straight or branched alkyl of from 1 to 6 carbon atoms, benzyl, or phenyl, —CO$_2$R$_3$ wherein R$_3$ is straight or branched alkyl of from 1 to 6 carbon atoms, or benzyl wherein the benzyl and phenyl groups can be unsubstituted or substituted by from 1 to 3 substituents each independently selected from halogen, CF$_3$, and nitro; and R is hydrogen or lower alkyl.

Especially preferred compounds of the invention is (4-Aminomethyl-tetrahydro-pyran-4-yl)-acetic acid and (4-Aminomethyl-tetrahydro-thiopyran-4-yl)-acetic acid.

Novel intermediates useful in the preparation of the final products are disclosed as well as a novel process for the preparation of the compounds.

DETAILED DESCRIPTION

The compounds of the instant invention and their pharmaceutically acceptable salts are as defined by Formula I.

The term "alkyl" is a straight or branched group of from 1 to 6 carbon atoms including but not limited to methyl, ethyl, propyl, n-propyl, isopropyl, butyl, 2-butyl, tert-butyl, pentyl, hexyl, and n-hexyl.

Lower alkyl is from 1 to 4 carbon atoms including but not limited to methyl, ethyl, propyl, n-propyl, isopropyl, butyl, n-butyl, isobutyl, and tertbutyl.

The benzyl and phenyl groups may be unsubstituted or substituted by from 1 to 3 substituents selected from halogen, $CF_3$, and nitro.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earit metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the invention may be synthesized, for example, by utilizing the general strategy (Scheme 1 below) outlined by Griffiths G., et al., *Helv. Chim. Acta*, 74:309 (1991). Alternatively, they may also be made as shown (in Scheme 2 below), analogously to the published procedure for the synthesis of 3-oxo-2,8-diazaspiro[4,5]decane-8-carboxylic acid tert-butyl ester (1) (Smith P. W., et al., *J. Med. Chem.*, 38:3772 (1995)). The compounds may also be synthesized by the methods outlined by Satzinger G., et al., (U.S. Pat. No. 4,024,175, and U.S. Pat. No. 4,152,326) (Schemes 3 and 4 below). In the case where X is $NR_1$ and R is $C(O)R_1$ or $CO_2R_3$, except where $R_3$ is a benzyl group, the compounds may be synthesized by the route outlined by Griffiths G., et al., *Helv. Chim. Acta*, 74:309 (1991) (Scheme 5 below). The compounds may also be synthesised by the method outlined in Scheme 6 below.

Scheme 1

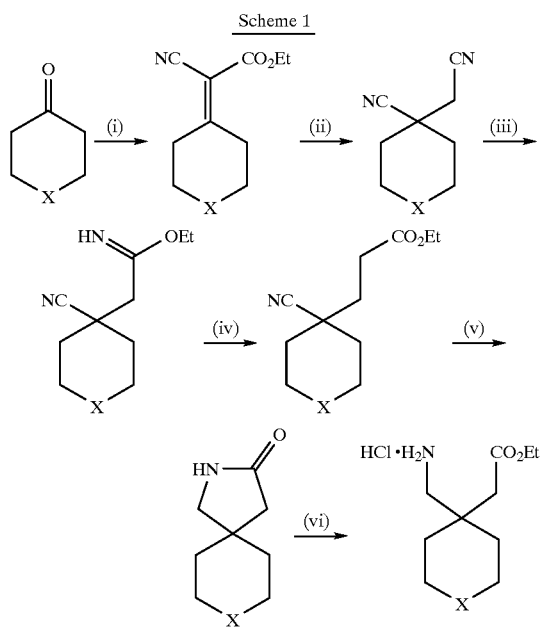

(i) Ethyl cyanoacetate, piperidine (Cope, et al., *J. Am. Chem. Soc.*, 63:3452 (1941))
(ii) NaCN, EtOH/$H_2O$,
(iii) EtOH, HCl
(iv) $H_2O/H^+$,
(v) $H_2$, Rh/C, MeOH,
(vi) HCl The X moiety can also be in the 3-position.

Scheme 2

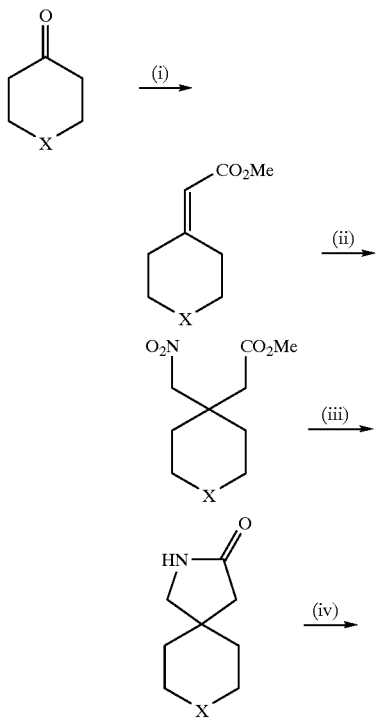

5
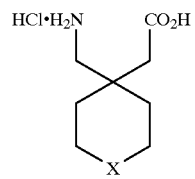
(i) Ph₃P=CHCO₂Me,
(ii) MeNO₂, 1,1,3,3-tetramethylguanidine,
(iii) Raney nickel, EtOH/H₂O,
(iv) HCl
6
The X moiety can also be in the 3-position.
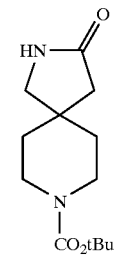
(1)
Scheme 3
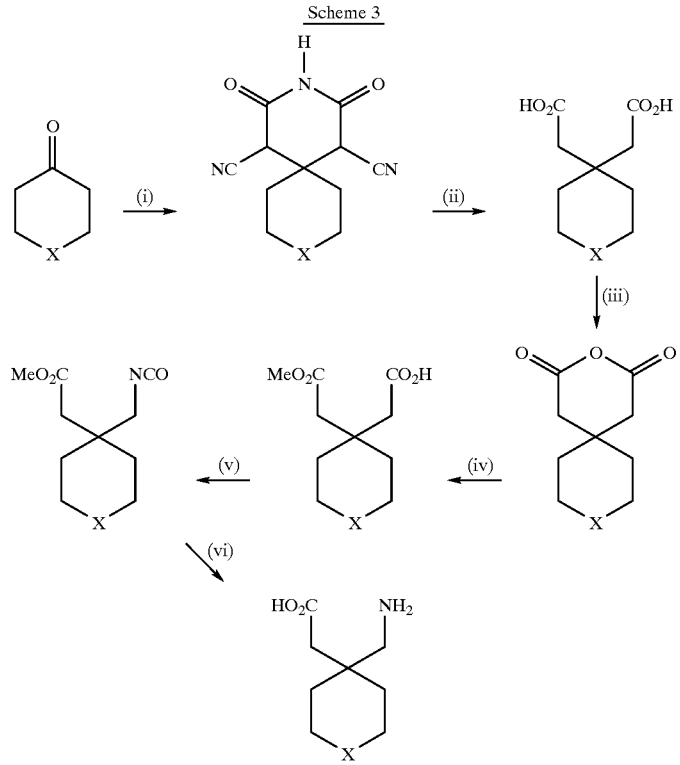
(i) Ethylcyanoacetate, ammonia then $H_3O^+$;
(ii) $H_2SO_4$;
(iii) $Ac_2O$;
(iv) MeOH;
(v) Curtius Reaction;
(vi) HCl, H₂O then anion exchange
The X moiety can also be in the 3-position.

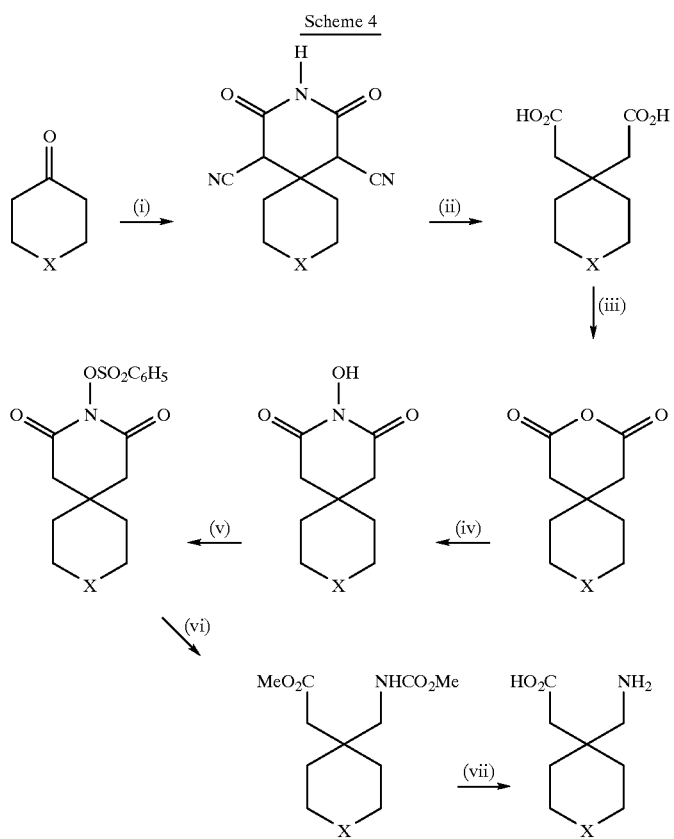
(i) Ethylcyanoacetate, ammonia then $H_3O^+$;
(ii) $H_2SO_4$;
(iii) $Ac_2O$;
(iv) $H_2NOH$;
(v) $PhSO_2Cl$;
(vi) $Et_3N$, MeOH;
(vii) HCl, $H_2O$ then anion exchange
The X moiety can also be in the 3-position.
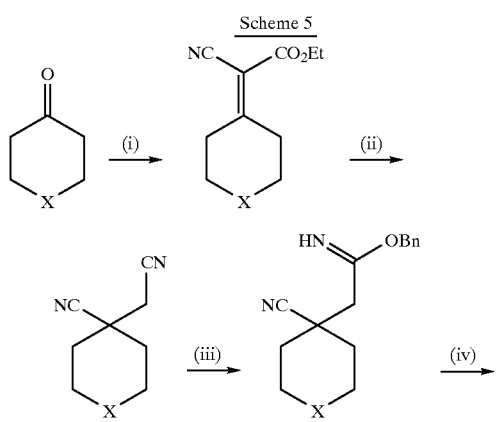
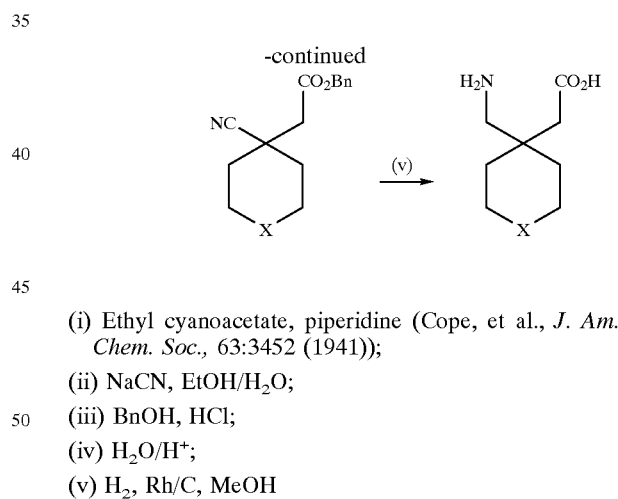
(i) Ethyl cyanoacetate, piperidine (Cope, et al., *J. Am. Chem. Soc.*, 63:3452 (1941));
(ii) NaCN, $EtOH/H_2O$;
(iii) BnOH, HCl;
(iv) $H_2O/H^+$;
(v) $H_2$, Rh/C, MeOH
The X moiety can also be in the 3-position.
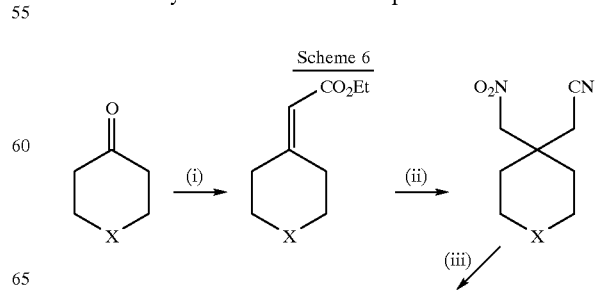

-continued

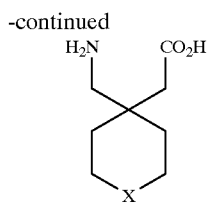

(i) $Ph_3P=CHCO_2Et$,
(ii) $MeNO_2$, tetramethylgaunidine,
(iii) $SnCl_2$, $HCl/H_2O$ The X moiety can also be in the 3-position.

The radioligand binding assay using [$^3$H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel", Gee N., et al., *J. Biological Chemistry*, in press).

TABLE 1

| Example No. | $IC_{50}$ ($\mu$M) | Number |
|---|---|---|
| 1 | 2.75 | 3 |
| 2 | 0.39 | 3 |

Table 1 above shows the binding affinity of Example 1 to the $\alpha_2\delta$ subunit. Gabapentin (Neurontin®) is about 0.10 to 0.12 $\mu$M in this assay. The compounds of the instant invention are expected, therefore, to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)-cyclohexaneacetic acid of structural formula

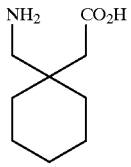

The compounds of the invention are also expected to be useful in the treatment of epilepsy. See Table 1 above for $IC_{50}$ data as compared to Neurontin®.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 28:901–905 (1989)).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 327:1–5 (1984)), was automated as previously described (Field, et al., Automation of the rat elevated X-maze test of anxiety. *Br. J. Pharmacol.*, 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signalled by chamber lights on and three 3-minute punished periods on fixed ratio 5 (by footshock concomitant to food delivery) signalled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 5:7–9 (1995)).

The compounds of the instant invention are also expected to be useful in treating the symptoms of manic, acute or chronic, single upside, or recurring. They are also expected to be useful in treating and/or preventing bipolar disorder (U.S. patent application Ser. No. 08/440,570 filed May 15, 1995).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

EXAMPLE 1

(4-Aminomethyl-tetrahydro-pyran-4-yl)-acetic Acid

Step 1: Cyanoacetate

A mixture of the ketone (48 mmol), ethyl cyanoacetate (48 mmol), ammonium acetate (4.9 mmol), and glacial acetic acid (9.6 mmol) were refluxed with a Dean Stark trap for 5 hours. The mixture was cooled and washed with $H_2O$. The $H_2O$ washes were extracted with toluene. The toluene extracts were combined with the original organic layer, dried over $MgSO_4$, and the solvent evaporated to give an orange crystalline solid (8.7 g). Yield 91%. A small sample was recrystallized from ethyl acetate; mp 48–58° C.

$^1$H NMR (CDCl$_2$) 400 MHz: δ 1.36 (3H, J=7.0 Hz), 2.80 (2H, t, J=5.4 Hz), 3.19 (2H, t, J=5.6 Hz), 3.80 (2H, t, J=5.4 Hz), 3.87 (2H, t, J=5.4 Hz), 4.29 (2H, q, J=5.7 Hz).

MS (CI) m/z: 137, 150, 168, 195, 196 (100% M+H$^+$), 197.

IR (CH$_2$Cl$_2$) $\upsilon_{max}$ cm-1: 2988, 2971, 2873, 2229, 1720, 1603, 1467, 1447, 1421, 1390, 1365, 1326, 1278, 1251, 1240, 1211, 1176, 1066, 1034, 1007, 863, 770.

Microanalysis: $C_{10}H_{13}NO_3.0.15\ H_2O$:

Calc'd: C, 60.69; H, 6.77; N, 7.08.

Found: C, 60.59; H, 6.62; N, 7.18.

Step 2: Binitrile

To a solution of NaCN (42 mmol) in 6 mL $H_2O$ and 160 mL ethanol (95%) was added the cyanoacetate (42 mmol). After 20 hours at reflux, the coiled solution was filtered, the filtrate acidified with gaseous HCl, and filtered again. The solvent was removed to give an impure orange solid (6.6 g). No further purification was attempted before the next step.

Step 3: Cyanoester

Hydrogen chloride gas was bubbled through an ice-cooled solution of the bis nitrile (2.1 g, 0.014 mol) dissolved in ethanol (100 mL). After standing for 3 days, the mixture was evaporated to dryness.

The residue was dissolved in ice/water and 1N HCl was added to pH 1. The aqueous solution was extracted with ethyl acetate and the extracts dried (over $MgSO_4$), filtered, and evaporated to dryness. Purification by column chromatography eluting with heptane/ethyl acetate 2:1 gave the final compound 0.8 g (30%) which was used without further purification.

Step 4: Lactam

A mixture of the cyanoester (0.8 g, 4.1 mmol), ethanolic ammonia (90 mL) and Raney nickel was shaken under hydrogen overnight. The mixture was filtered and the liquor evaporated to dryness. Trituration with ether gave the product 0.55 g (87%), mp 125–127° C.

$^1$H NMR (CDCl$_3$) 400 MHz: δ 1.60–1.70 (m, 4H), 2.29 (s, 2H), 3.25 (s, 2H), 3.60–3.75 (m, 4H), 5.85 (bs, 1H).

IR (film) $\upsilon_{max}$ cm$^{-1}$: 3190, 3100, 2971, 2935, 2852, 1687, 1102.

MS (CI) m/z: 156 (100%) M+H$^+$.

Microanalysis: $C_8H_{13}NO_2$:

Calc'd: C, 61.91; H, 8.44; N, 9.03.

Found: C, 61.57; H, 8.35; N, 8.75.

Step 5: (4-Aminomethyl-tetrahydro-pyran-4-yl)-acetic Acid

The lactam (0.45 g, 2.6 mmol) was refluxed in 12N HCl (20 mL) for 24 hours. The aqueous phase was washed with ethyl acetate and then evaporated to dryness. The residue was recrystallized from methanol/ether to give the required product 0.29 g (53%), mp 180–183° C.

$^1$H NMR (d$_6$-DMSO) 400 MHz: δ 1.40–1.60 (m, 4H), 2.53 (s, 2H), 3.02 (s, 2H), 3.50–3.70 (m, 4H), 8.02 (s, 3H), 12.45 (bs, 1H).

IR (film) $\upsilon_{max}$ cm$^{-1}$: 2936, 1712, 1611, 1514, 1398, 1191, 1101, 1026.

MS (ES) m/z: 174 (95%) M+H$^+$.

Microanalysis: $C_8H_{15}NO_3.HCl.0.1\ H_2O$:

Calc'd: C, 45.44; H, 7.72; N, 6.62.

Found: C, 45.46; H, 8.07; N, 6.26.

EXAMPLE 2

(4-Aminomethyl-tetrahydro-thiopyran-4-yl)-acetic Acid

Step 1: Unsaturated Ethyl Ester

A solution of tetrahydrothiopyran-4-one (2.5 g, 21.6 mmol) and (carbethoxymethylene) triphenylphosphorane (9.0 g, 25.9 mmol) was heated to reflux in toluene for 18 hours. The mixture was cooled and evaporated to dryness. The residue was purified by flash chromatography (silica, ether/hexane 1:1) to give the required product as an oil (3.77 g).

Yield 94%.

$^1$H NMR (CDCl$_3$) 400 MHz: δ 1.28 (3H, t, J=7.2 Hz), 2.50–2.55 (2H, m), 2.74–2.80 (4H, m), 3.18–3.21 (2H, m), 4.15 (2H, q, J=7.2 Hz), 5.67 (1H, s).

IR (film) $\upsilon_{max}$ cm$^{-1}$: 1649, 1713, 2908, 2981.

MS (CI) m/z: 187 (15%) M+H⁺.

Step 2: Nitro Ester

The unsaturated ethyl ester (1.0 g, 5.3 mmol) was heated to reflux under nitrogen in nitromethane (50 mL) with tetramethylguanidine (0.5 mL) for 10 hours. After allowing the mixture to cool to room temperature, it was diluted with ethyl acetate and washed with 1N HCl. The organic solution was separated, dried (magnesium sulfate) and the solvent removed in vacuo. The residue was purified by flash chromatography to give a colorless oil (0.41 g).

Yield 31%.

$^1$H NMR (CDCl$_3$) 400 MHz: δ 1.28 (3H, t, J=7.2 Hz), 1.85–2.00 (4H, m), 2.54 (2H, s), 2.60–2.75 (4H, m), 4.17 (2H, q, J=7.2 Hz), 4.72 (2H, s).

IR (film) $\upsilon_{max}$ cm$^{-1}$: 1374, 1458, 1549, 1728.

MS (El) m/z: 247 (100%) M$^1$.

Step 3: (4-Aminomethyl-tetrahydro-thiopyran-4-yl)-acetic Acid

The nitro ester (0.4 g, 1.62 mmol) was dissolved in concentrated hydrochloric acid with tin (II) chloride (1.5 g). The mixture was heated to 100° C. for 2 hours. The mixture was then evaporated to dryness. The residue was purified by reverse phase chromatography to give colorless crystals (0.10 g).

Yield 26%.

$^1$H NMR (d$_6$-DMSO) 400 MHz: δ 1.65–1.80 (4H, m), 2.44 (2H, s), 2.54–2.67 (4H, m), 2.95 (2H, s), 7.99 (3H, br s), 12.42 (1H, br s).

IR (film) $\upsilon_{max}$ cm$^{-1}$: 1525, 1582, 1712, 2959, 3382.

Microanalysis: C$_8$H$_{15}$NO$_2$S.HCl.0.75 H$_2$O:

Calc'd: C, 40.16; H, 7.37; N, 5.86.

Found: C, 40.39; H, 7.31; N, 5.98.

We claim:

1. A compound of formula

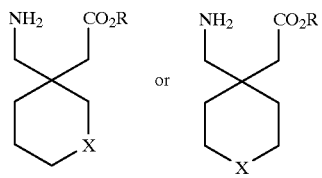

I or a pharmaceutically acceptable salt thereof wherein:

X is O, S, S(O), S(O)$_2$, or NR$_1$ wherein R$_1$ is hydrogen, straight or branched alkyl of from 1 to 6 carbon atoms, benzyl, —C(O)R$_2$ wherein R$_2$ is straight or branched alkyl of from 1 to 6 carbon atoms, benzyl, or phenyl, or —CO$_2$R$_3$ wherein R$_3$ is straight or branched alkyl of from 1 to 6 carbon atoms, or benzyl wherein the benzyl and the phenyl groups can be unsubstituted or substituted by from 1 to 3 substituents each independently selected from halogen, CF$_3$, and nitro; and R is hydrogen or lower alkyl.

2. A compound according to claim 1 wherein X is O.

3. A compound according to claim 1 wherein X is S.

4. A compound according to claim 1 wherein X is S(O).

5. A compound according to claim 1 wherein X is S(O)$_2$.

6. A compound according to claim 1 wherein X is NR$_1$, wherein R$_1$ is hydrogen, straight or branched alkyl of from 1 to 6 carbon atoms, benzyl, —C(O)R$_2$ wherein R$_2$ is straight or branched alkyl of from 1 to 6 carbon atoms, benzyl, or phenyl, —CO$_2$R$_3$ wherein R$_3$ is straight or branched alkyl of from 1 to 6 carbon atoms, or benzyl.

7. A compound according to claim 6 wherein X is NH.

8. A compound according to claim 6 wherein X is NR$_1$ wherein R$_1$ is straight or branched alkyl of from 1 to 6 carbon atoms or is benzyl.

9. A compound according to claim 6 wherein X is NR$_1$ wherein R$_1$ is —C(O)R$_2$ wherein R$_2$ is straight or branched alkyl of from 1 to 6 carbon atoms, benzyl, or phenyl.

10. A compound according to claim 6 wherein X is —CO$_2$R$_3$ wherein R$_3$ is straight or branched alkyl of from 1 to 6 carbon atoms or benzyl.

11. A compound named (4-Aminomethyl-tetrahydropyran-4-yl)-acetic acid or (4-Aminomethyl-tetrahydrothiopyran-4-yl)-acetic acid.

12. A pharmaceutical composition comprising a therapeutically effective amount of a compound according to claim 1 and a pharmaceutically acceptable carrier.

13. A method for treating epilepsy comprising administering a therapeutically effective amount of a compound according to claim 1 to a mammal in need of said treatment.

14. A method for treating faintness attacks, hypokinesia, and cranial disorders comprising administering a therapeutically effective amount of a compound according to claim 1 to a mammal in need of said treatment.

15. A method for treating neurodegenerative disorders comprising administering a therapeutically effective amount of a compound according to claim 1 to a mammal in need of said treatment.

16. A method for treating depression comprising administering a therapeutically effective amount of a compound according to claim 1 to a mammal in need of said treatment.

17. A method for treating anxiety comprising administering a therapeutically effective amount of a compound according to claim 1 to a mammal in need of said treatment.

18. A method for treating panic comprising administering a therapeutically effective amount of a compound according to claim 1 to a mammal in need of said treatment.

19. A method for treating pain comprising administering a therapeutically effective amount of a compound according to claim 1 to a mammal in need of said treatment.

20. A method for treating neuropathological disorders comprising administering a therapeutically effective amount of a compound according to claim 1 to a mammal in need of said treatment.

* * * * *